US011576598B2

(12) United States Patent
Imran

(10) Patent No.: US 11,576,598 B2
(45) Date of Patent: Feb. 14, 2023

(54) APPARATUS, SYSTEMS AND METHODS FOR SENSING BLADDER FULLNESS

(71) Applicant: InCube Labs, LLC, San Jose, CA (US)

(72) Inventor: Mir A. Imran, Los Altos Hills, CA (US)

(73) Assignee: InCube Labs, LLC, San Jose, CA (US)

(*) Notice: Subject to any disclaimer, the term of this patent is extended or adjusted under 35 U.S.C. 154(b) by 625 days.

(21) Appl. No.: 16/536,197

(22) Filed: Aug. 8, 2019

(65) Prior Publication Data

US 2020/0046278 A1    Feb. 13, 2020

Related U.S. Application Data

(60) Provisional application No. 62/715,983, filed on Aug. 8, 2018.

(51) Int. Cl.
*A61B 5/20* (2006.01)
*A61B 5/00* (2006.01)
(Continued)

(52) U.S. Cl.
CPC .............. *A61B 5/208* (2013.01); *A61B 5/204* (2013.01); *A61B 5/205* (2013.01); *A61B 5/0031* (2013.01);
(Continued)

(58) Field of Classification Search
CPC ......... A61B 5/208; A61B 5/204; A61B 5/205; A61B 5/0031; A61B 5/03; A61B 5/036;
(Continued)

(56) References Cited

U.S. PATENT DOCUMENTS 3,810,259 A * 5/1974 Summers .............. A61F 2/0036
128/DIG. 25
5,058,591 A    10/1991 Companion et al.
(Continued)

FOREIGN PATENT DOCUMENTS

| AU | 2013224644 A1 | 9/2013 |
| WO | WO-2018184962 A1 | 10/2018 |
| WO | WO-2020033775 A1 | 2/2020 |

OTHER PUBLICATIONS

International search report with written opinion dated Oct. 11, 2019 for PCT/US2019/045814.
(Continued)

*Primary Examiner* — Sean P Dougherty
(74) *Attorney, Agent, or Firm* — Brooks Kushman P.C.

(57) ABSTRACT

Embodiments of the invention provide devices and systems to monitor fullness of a patient's bladder. One embodiment of a bladder fullness (BF) measure system comprises a sensor device (SD) and a controller. The SD generates an output signal (OS) based on the force exerted by the bladder against SD the wherein the OS corresponds to a degree of BF. The SD may be attached to the bladder wall or adjoining tissue and positioned between the bladder and the pubic bone such that the SD is not affected by tissues force other than that from the bladder. The controller connects to the SD and causes an associated implant to perform a function when the SD output signal exceeds a predetermined threshold. Embodiments are particularly useful for providing information on BF to patients suffering from spinal injury or other conditions whereby they have lost the ability to sense BF and/or voluntarily urinate.

26 Claims, 9 Drawing Sheets

(51) Int. Cl.
 *A61B 5/03* (2006.01)
 *G01L 19/00* (2006.01)
(52) U.S. Cl.
 CPC .............. *A61B 5/03* (2013.01); *A61B 5/036* (2013.01); *A61B 5/4222* (2013.01); *A61B 5/6874* (2013.01); *A61B 2562/0219* (2013.01); *A61B 2562/0247* (2013.01); *G01L 19/0092* (2013.01)
(58) Field of Classification Search
 CPC .............. A61B 5/4222; A61B 5/6874; A61B 2562/0219; A61B 2562/0247; G01L 19/0092
 See application file for complete search history.

(56) References Cited

U.S. PATENT DOCUMENTS

| | | | | |
|---|---|---|---|---|
| 6,117,086 | A * | 9/2000 | Shulze | A61B 5/03 73/706 |
| 6,491,647 | B1 * | 12/2002 | Bridger | G01L 1/2231 128/900 |
| 6,939,299 | B1 * | 9/2005 | Petersen | A61B 3/16 600/587 |
| 8,412,294 | B2 | 4/2013 | Stothers et al. | |
| 9,672,393 | B1 * | 6/2017 | Zhu | A61N 1/3787 |
| 10,471,255 | B2 | 11/2019 | Imran | |
| 2008/0139959 | A1 * | 6/2008 | Miethke | A61B 5/0031 600/561 |
| 2010/0030297 | A1 | 2/2010 | Gerber et al. | |
| 2010/0228079 | A1 * | 9/2010 | Forsell | A61B 17/12009 600/30 |
| 2011/0040206 | A1 * | 2/2011 | Burger | A61B 5/6846 600/561 |
| 2011/0066046 | A1 * | 3/2011 | Young | A61B 5/02241 600/486 |
| 2011/0203390 | A1 * | 8/2011 | Tao | G06F 3/0414 73/862.046 |
| 2012/0010535 | A1 * | 1/2012 | Kubiak | A61B 5/1036 600/592 |
| 2013/0098170 | A1 * | 4/2013 | Lee | G01L 9/007 73/862.626 |
| 2013/0109990 | A1 * | 5/2013 | Akingba | A61B 5/113 600/529 |
| 2013/0158436 | A1 * | 6/2013 | Kocjancic | A61B 5/03 600/587 |
| 2014/0005569 | A1 * | 1/2014 | Miethke | G01L 19/0046 72/347 |
| 2014/0155710 | A1 * | 6/2014 | Rowland | A61B 5/0215 600/302 |
| 2014/0249595 | A1 | 9/2014 | Chancellor et al. | |
| 2015/0045609 | A1 * | 2/2015 | Anderson | A61F 2/004 600/31 |
| 2015/0057523 | A1 * | 2/2015 | Gunn | A61B 3/16 141/2 |
| 2016/0029956 | A1 * | 2/2016 | Rowland | G01L 19/0038 600/300 |
| 2016/0270678 | A1 * | 9/2016 | Swoboda | A61B 5/031 |
| 2016/0287101 | A1 * | 10/2016 | Tai | A61B 5/03 |
| 2016/0331949 | A1 * | 11/2016 | Lutz | A61M 27/006 |
| 2016/0346160 | A1 * | 12/2016 | Forsell | A61N 1/3787 |
| 2016/0354028 | A1 * | 12/2016 | Damaser | A61N 1/3606 |
| 2016/0365198 | A1 * | 12/2016 | Pan | H01G 5/38 |
| 2017/0219450 | A1 * | 8/2017 | Swoboda | A61B 5/02156 |
| 2017/0258386 | A1 | 9/2017 | Woltjer et al. | |
| 2017/0325926 | A1 * | 11/2017 | Lamraoui | G16H 40/63 |
| 2018/0028824 | A1 * | 2/2018 | Pivonka | A61N 1/36125 |
| 2018/0042712 | A1 * | 2/2018 | Sufyan | A61F 2/0045 |
| 2018/0160922 | A1 * | 6/2018 | Arnold | A61B 5/74 |
| 2018/0325454 | A1 * | 11/2018 | Petelenz | A61B 5/447 |
| 2019/0209067 | A1 | 7/2019 | Peterson et al. | |
| 2019/0307997 | A1 * | 10/2019 | Auvray | A61B 5/031 |

OTHER PUBLICATIONS

Extended European Search Report re Europe App. No. 19848606 dated Mar. 10, 2022.

* cited by examiner

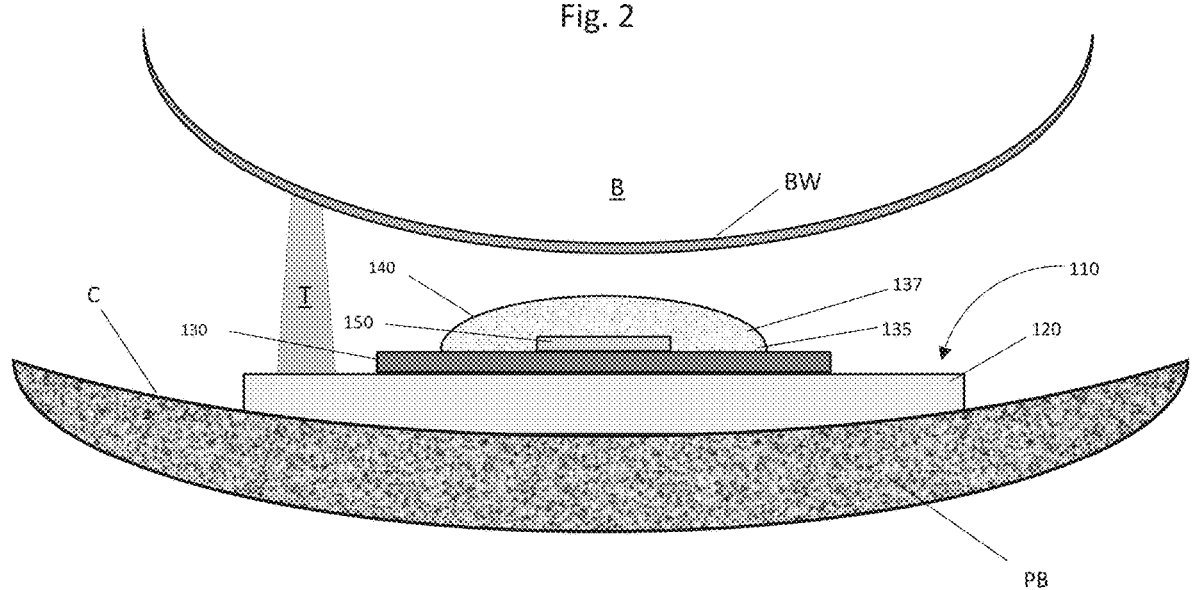

APPARATUS, SYSTEMS AND METHODS FOR SENSING BLADDER FULLNESS

RELATED APPLICATIONS

This application claims the benefit of priority to U.S. Provisional Patent Application No. 62/715,983, entitled "Apparatus, Systems and Methods For Sensing Bladder Fullness", filed Aug. 8, 2018; the aforementioned priority application being incorporated by reference herein for all purposes.

BACKGROUND OF THE INVENTION

1. Field of the Invention

Embodiments of the invention relate to medical apparatuses and methods. More particularly, embodiments of the invention relate to systems, devices, apparatus, and sensors for measuring real-time information regarding bladder fullness. Still, more particularly, embodiments of the invention relate to systems and methods for providing real-time information on bladder fullness to patients who have lost bladder control to allow them to selectively control urinary function utilizing such information.

Many disorders can result in loss of a patient's ability to voluntarily control bladder function. Most commonly, patients suffering from spinal cord injuries can lose not only the ability to voluntarily control urination, but also the ability to sense when the bladder is full. Such patients have usually had to rely on the chronic use of a Foley catheter which is placed through the urethra and has a distal tip residing in the bladder. However, the use of Foley catheters for these patients has a number of drawbacks. In particular, the use of Foley catheters for these patients presents a constant risk of infection of the patient's urinary tract which is exacerbated by the frequent need to exchange for a new catheter. Moreover, Foley catheters usually drain into a bag which the patient must carry when away from home or a treatment facility. The need to carry the drain bag is a significant burden to many patients.

To at least partially overcome these problems, very promising new systems have been proposed which allow patients and their caregivers to selectively stimulate the pudendal or other nerves to control voiding of the bladder. Such systems can eliminate the need for Foley catheters and are described, for example, in US Patent Publication 2014/0249595, the full disclosure of which is incorporated herein by reference.

While a significant advance, such nerve stimulation systems do not alert the patient when their bladder is full. Since many patients will have lost the ability to sense when the bladder is full, these patients may prolong periods between voiding, raising the pressure in the bladder above safe levels and risking injury and infection of the kidneys.

For these reasons, it would be desirable to provide systems and devices which provide feedback to a patient or caregiver regarding fullness of the patient's bladder.

SUMMARY OF THE INVENTION

Various embodiments of the invention provide apparatus, systems and methods for providing information including real time information on the degree of fullness of a patient's bladder. In particular embodiments, the apparatus/system is able to measure a degree of fullness of the patient's bladder. The apparatus includes a sensor, typically a pressure sensor which is able to sense an amount of force applied to the apparatus by the bladder. According to one or more embodiments, the apparatus and/or system may be configured to generate information for a control system such as a closed loop system that is used to initiate and control voiding of the bladder. Such a control system can be configured to receive a signal (electrical/analog or digital) from the sensor representative of bladder volume and use that signal to void the bladder when the pressure sensor signal goes beyond a threshold value. The trigger threshold may be based on the percent change in the signal generated by the pressure sensor between pre-determined bladder volumes representing "empty" and "full." This percent change will henceforth be referred to as delta or Δ. A large Δ provides for better efficacy of the bladder fullness measurement (BFM) apparatus in terms of its use with an associated bladder control system.

One advantage of the BFM apparatus over other sensor technologies to determine bladder fullness is that the BFM apparatus does not need to be positioned within the bladder by catheterization that is, it does not need to be attached to a Foley catheter or other urinary drainage device that is permanently left in place in the patient's urinary tract (this is advantageous since it reduces the risk of infection associated with Foley catheters or other like urinary drainage device). Instead, in various embodiments, the BFM apparatus can be attached directly to the bladder wall (e.g., using a suture or other attachment means known in the medical arts). Also, according to some embodiments, it may be implanted with an associated electrical stimulation system (e.g., a pulse generator) configured to provide for electrically evoked urination based on a signal(s) received from the BFM apparatus and then function without any further action required by the patient.

In various configurations, embodiments of the BFM apparatus can be configured to be attached to the bladder and positioned between the bladder wall and the pubic bone so that the pressure sensor is only effected by force exerted by the bladder wall (e.g., due to degree of fullness) and remains substantially unaffected by force exerted by other tissue (e.g., from the intestines). In particular embodiments, the BFM apparatus can be sutured to the connective tissue adjacent the bladder wall. In use, such embodiments provide the advantage of reducing signal noise or motion artifact resulting from movement of other organs or tissue (e.g., the intestines, lungs, heart, etc.) besides the bladder. This in turn improves both the accuracy and precision of measurements of bladder fullness. Another advantage of the BFM apparatus is that its power source does not require high voltage or magnetic fields. Thus, it can be powered by a low voltage long lasting battery which may be configured to be rechargeable by induction coupling with a charging device placed on or near the surface of the abdomen.

Various embodiments of the bladder sensor may be used to provide information for monitoring bladder fullness for a variety of uses. For example, according to one embodiment, information provided by the sensor may be used by a physician to assess the patient's bladder function and diagnose related conditions such as neuropathy or damage of the nerves controlling bladder function (e.g., the pudendal nerve), overactive bladder, incontinence and related conditions. In additional embodiments, the bladder sensor may form part of a closed-loop neuro-stimulation system which can be used to provide neuro-stimulation therapy to treat one more urinary related conditions. Such neuro-stimulation therapy can be used for a number of functions including for example, urination initiation and control, to prevent or reduce overactive bladder or to increase pelvic floor muscle tone or urinary sphincter pressure, or both, and thereby prevent involuntary urine leakage.

Embodiments of the invention are particularly useful for monitoring and providing information on the degree of fullness of a patient's bladder particularly for those patients who have lost the ability to sense bladder fullness and/or voluntarily urinate due to spinal cord injury or other condition affecting the functionality of one or more of their spinal cord, pudendal nerves, or other neural pathway involved in the urination process.

The invention also contemplates a neuro-stimulation system and method that make use of such a BFM apparatus for alleviation of urinary incontinence. The BFM apparatus may be able to detect the fill stage or contraction of the bladder at any given time, and provide signals indicating such conditions to components of the neuro-stimulation system such as an implanted neuro-stimulator, an external programmer or a data recorder.

In one aspect, the invention provides a bladder sensor apparatus for sensing or monitoring fullness of the patient's bladder comprising a base which comprises a flexible material, a rigid layer attached to the base, a deformable membrane positioned over and hermetically sealed to the rigid layer, and a pressure sensor. The base is configured to be positioned in and attached to tissue between the pubic bone and the bladder and to conform to a contour of the pubic bone so as to be mechanically supported by the public bone. In particular embodiments, the bases is positioned near the pubic bone such that mechanical support provided by the pubic bone to the base prevents the membrane from being substantially deformed by force from tissue other than the bladder.

The rigid layer may comprise various metals (e.g., stainless steel) or rigid polymers known in the art, though desirably at least a portion of the rigid layer comprises a conductive material such as a metal or conductive polymer. The deformable membrane, which is sealed to the rigid layer defines a cavity between the membrane and the rigid layer. The cavity is filled with a fluid such a mineral oil or silicone. The membrane is positioned and configured to deform from force exerted by the bladder against the membrane so as to exert a pressure on the fluid, with the pressure correlated to a degree of fullness of the bladder. The deformability of the membrane may be achieved by the selection of its dimensions and the use of various deformable materials known in the art such as metals and polymers including, various elastomers known in the art.

The pressure sensor is positioned on a portion of the rigid layer within the cavity such that it is able to measure the pressure of the fluid within the cavity. The sensor generates a signal (electrical or digital) correlated to the pressure within the cavity which is in turn is correlated to a degree of fullness of the bladder. It is electrically coupled to the conductive portion of the rigid layer such that signals generated by the pressure sensor can be transmitted to via the conductive portion to a controller or other electrical circuitry. It may be attached to the rigid layer via various adhesives known in the art and may be electrically coupled to the conductive portion by solder or other electrically conductive means. According to various embodiments, the pressure sensor may correspond to one or more of a strain gauge, a solid state sensor or a MEMS-based sensor. Also, according to some embodiments, the sensor may comprise a plurality of sensors, positioned in one or more locations within the cavity.

In some embodiments, the BFM apparatus or system may include an accelerometer for sensing an orientation or position of the patient which may affect one or more of bladder pressure and/or a bladder fullness measurement. Typically, the accelerometer will be operatively coupled to the controller such that a signal(s) generated by the accelerometer are received by the controller. The controller can include logic for using the signals from the accelerometer to detect whether the patient is in a particular position, for example, supine sitting, standing, or bent-over position. The controller may then make adjustments for an amount of bladder fullness resulting in a notice or alert being sent to the patient, e.g., regarding bladder fullness, need to urinate etc. In particular embodiments, the controller includes logic to account for sudden changes in the patient's orientation such that during that time signals from the BFM apparatus sensor are: i) gated out or otherwise not used by the controller in the determination of bladder fullness during the orientation change and fixed period afterward; ii) are adjusted to reduce their impact on bladder fullness determination by the controller; and/or iii) are taken over a longer sampling period in making a bladder fullness by determination by the controller whenever an orientation change is detected. According to various embodiments, the accelerometer may be directly affixed to the BFM apparatus, for example, to the base, or may be positioned external to the BFM apparatus and either coupled by wire or wirelessly. For external positioning embodiments, the accelerometer may either be implanted or worn externally by the patient.

In another aspect, the invention provides a method for monitoring the fullness of a bladder of a patient using one or more embodiments of the bladder fullness measurement (BFM) apparatus described herein. The method comprises positioning an embodiment of the BFM apparatus between the patient's pubic bone and the bladder such that the pressure sensor is subjected to force from the patient's bladder (due to its degree of fullness) but not substantially effected by force from tissue other than that from the bladder. In many embodiments, this can be accomplished by positioning the back or base of the BFM apparatus so that it faces the pubic bone such that the base is mechanically supported by the pubic bone. Desirably, though not necessarily, the BFM apparatus is fixedly attached to the wall of the patient's bladder or to connective tissue such as fascia. This can be accomplished by suturing the base to the fascia via one or more suture holes in the base or other location on the apparatus. Also, through the use of conformable materials, the base of the apparatus can be conformed or otherwise shaped by the surgeon to the curve of the patient's pubic bone to use the patient's pubic bone as one approach to shield the sensor apparatus from tissue forces other than that from the bladder. The base may be pre-bent before implantation to contour matching that of the pubic bone or at the time of the implantation.

In particular embodiments, the BFM apparatus may be positioned in a pocket created by the surgeon in the fascia between the pubic bone and the bladder wall. In one approach for doing this, the surgeon creates the pocket and then slides the apparatus in the pocket and then sutures the base of the apparatus to the connective tissue. This thickness of the apparatus and the base can be selected such that the surgeon need only create a pocket of around 1 cm or less though, larger dimensions are also contemplated.

Once positioned at a selected location in tissue between the patient's pubic bone and bladder, the BFM apparatus may be coupled to a controller which receives signals from the BFM apparatus corresponding to an amount of fullness of the bladder. In particular embodiments, the controller may be part of otherwise operably coupled to a closed loop urination control system. The BFM apparatus may be implanted in an on-state or switched on once implanted. Once implanted and activated the BFM apparatus sends a signal (e.g., an output signal) corresponding to the degree of distension or fullness of the bladder to the controller (the degree of distention being synonymous with or otherwise correlated to the degree of fullness of the bladder). The controller then uses that signal to perform one or more functions which may involve or relate to the patient's urinary function. In particular embodiments, the bladder fullness signal is used by the controller to initiate urination using the closed loop urinary control system.

In various embodiments, the BFM apparatus may be implanted in a pre-calibrated state or may be calibrated after implantation as is discussed herein. It may also be implanted in an on-state or switched on once implanted. Once implanted and activated, the BFM apparatus sends a signal to the controller corresponding to the degree of distension/fullness of the bladder. For embodiments that involve post implant calibration, logic (e.g., programming) used by the controller may be updated with the calibration value. The controller then uses that signal to perform one or more functions which typically will relate to or involve the patient's urinary function. According to one or more embodiments, the functions may include causing an associated implant (e.g., an implanted pulse generator or other neuro-stimulation device) to perform a function (e.g. stimulation of the pudendal nerve) or sending a notification or alert to the patient. The notification or alert may be sent to the patient for example via a cell phone or PDA device operably coupled to or otherwise in communication with the controller (e.g., via RF communication). The notification or alert may be related to one or more of the following: the degree of fullness of the bladder, an estimated time when the bladder will be full, and a need to urinate based on the degree of bladder fullness. The alert on the need to urinate may include a ranking of the need to urinate, such as immediately (e.g., next five minutes), moderate (e.g., next five to ten minutes), or low (e.g., next 15 to 30 minutes).

In one or embodiments, the BFM apparatus or system may be calibrated after implantation so as to calibrate the signal (electrical/analog or digital) generated by the BFM apparatus to a degree of fullness of the bladder. In one implementation, this can be accomplished by filling the bladder with a known volume(s) of fluid using a bladder access device such as a Foley or other urinary drainage catheter known in the art and then measuring the signal (electrical or digital) produced by the apparatus in response to the degree of fullness. A calibration curve can be developed and data can be then downloaded to the controller or other logic resources coupled to the BFM apparatus or system. Typically, several calibrations will be done over the first several months after implantation. The first may be done soon after implantation and then subsequent calibrations may be done several months after implantation to account for a wound healing response in around the implanted BFM apparatus which may affect the deformability of the deformable membrane and/or the amount of force exerted by the bladder against the BFM apparatus in particular to the membrane.

In embodiments where the BFM apparatus includes an accelerometer the controller can include logic for using the signal from the accelerometer to detect whether the patient is in a particular position, for example, supine sitting, standing, or bent-over position. Based on the position, the controller may then make adjustments for an amount of bladder fullness resulting in a notice or alert being sent to the patient, e.g., regarding bladder fullness, need to urinate, etc. In use, such embodiments, provide for more accurate message being sent to the patient regarding the bladder and/or urination urgency status. In cases of the bent-over position, the controller may also send the patient an alert to sit up due to the increased pressure put on the bladder from being put in the bent-over position. The reasons being that such pressure my possibly result in urinary linkage (incontinence) or urine being forced back into the kidneys. In this way, embodiments of the invention including an accelerometer, provide for the reduced possibility of damage to the kidney as well as urinary leakage for patients who have lost the ability to urinate due to spinal injury or other condition.

For a fuller understanding of the nature and advantages of the present invention, reference should be made to the following detailed description taken in conjunction with the accompanying drawings. The drawings represent embodiments of the present invention by way of illustration. Accordingly, the drawings and descriptions of these embodiments are illustrative in nature and not restrictive.

BRIEF DESCRIPTION OF THE DRAWINGS

FIG. 2 illustrates a side view of an embodiment of the BFM apparatus of FIG. 1.

FIG. 3A is a perspective view showing placement of the BFMA within the pelvic area of the patient; FIG. 3B is a side view illustrating placement of the BFMA between the bladder and the pubic bone.

FIG. 4A shows creation of the pocket; FIG. 4B shows the advancement of the BFMA into pocket; FIG. 4C shows positioning of the BFMA at a desired tissue site within the pocket; and FIG. 4D shows the BFMA sutured in place at the tissue site and connection of the BFMA to an implanted controller.

DETAILED DESCRIPTION OF THE INVENTION

Figure 1:
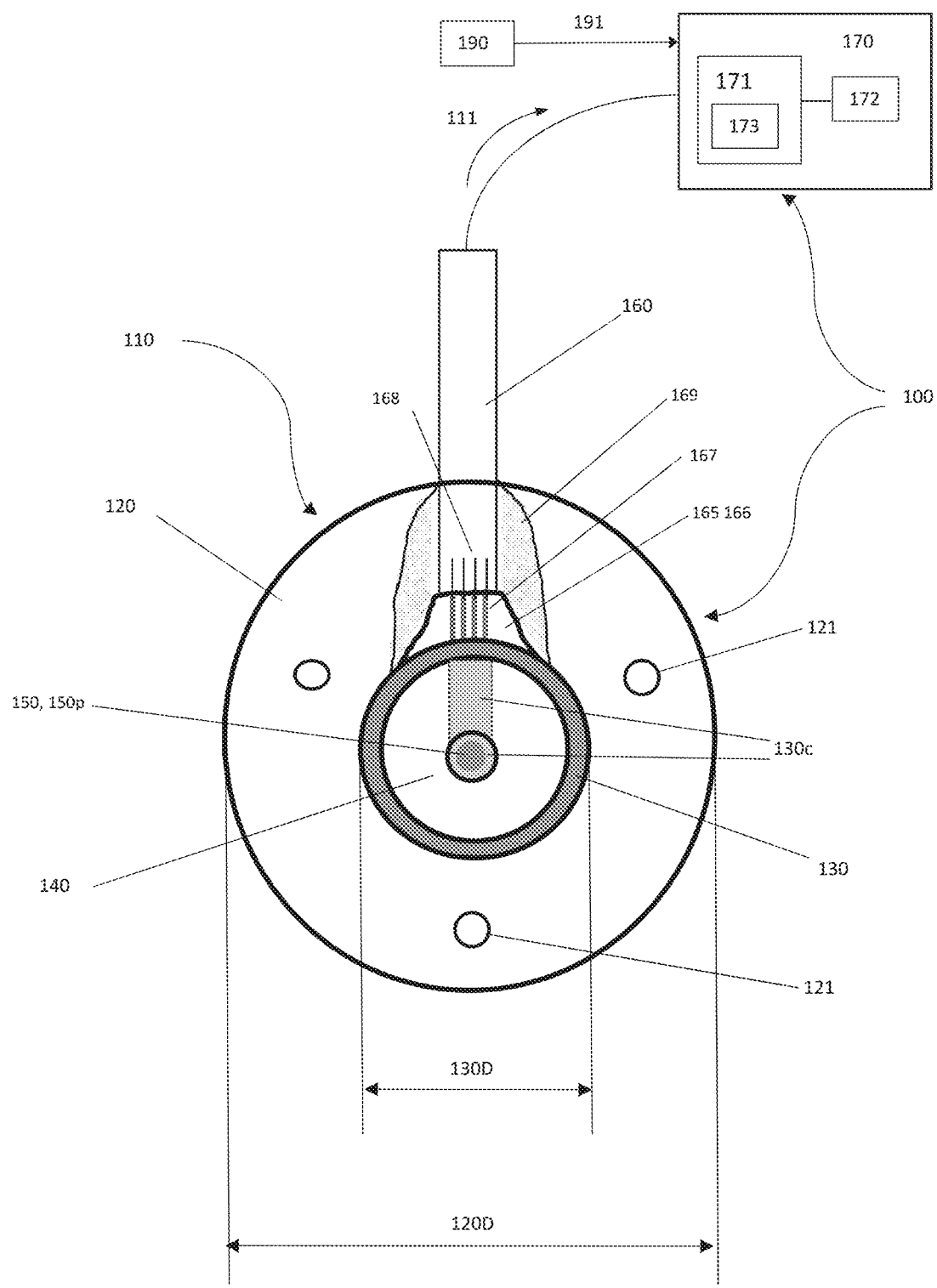
FIG. 1 is a top view of an embodiment of a bladder fullness measurement (BFM) apparatus.

Embodiments of the invention provide devices, systems, and methods for measuring bladder fullness in a patient and providing information on such. Particularly, embodiments provide an apparatus and a system for measuring and providing real-time information relating to the patient's bladder fullness (from urine) based on bladder fullness due to urine volume. The amount of bladder fullness is correlated to the amount of bladder distention and accordingly, as used herein, the two terms are considered synonymous. Also, as used herein the term, "about" means within ±10% of a stated property, dimension, or other value and, more preferably, ±5% of the stated value. Also, as used herein, the term "substantially" means within ±10% of a stated property or quality and where appropriate within a numerical value of a stated property or quality, more preferably, ±5% of the stated property or quality.

Various embodiments of the invention provide sensors, apparatus and systems for monitoring the bladder for degree and/or signs of fullness (i.e., due to contained urine) and providing information to the patient on the degree and/or signs of bladder fullness. Some embodiments provide an apparatus for continuously monitoring the bladder for degree and/or signs of fullness in order to initiate urination (aka micturition) for patients who have lost voluntary bladder control and/or the ability to sense bladder fullness such as patients who have sustained a spinal cord injury. Accordingly, various embodiments of the apparatus provided can be configured to function as a bladder fullness measurement (BFM) apparatus to allow the patient and/or urinary control implant to utilize information provided by the sensor on bladder fullness to initiate or trigger micturition. Embodiments of the BFM apparatus provide the advantage of eliminating the need for the patient to perform voiding at timed intervals by providing an output signal representative of current bladder volume directly to the patient or an associated implant or system which the patient or system can then use to initiate micturition and void the bladder.

According to one or more embodiments, signals generated by the BFM apparatus may be used to notify the patient of a degree of bladder fullness including, for example, full bladder status. The information provided by the signal can then be used by the patient to allow them to self-void or trigger an associated bladder control system having an implant to deliver electrical stimulation to the pudendal nerve or other tissue, to initiate voiding of the bladder when the bladder is full. One such bladder control system is described in U.S. patent application Ser. No. 15/410,692, entitled Systems And Methods For Patient-Enabled Bladder Control which is incorporated by reference herein for all purposes. Embodiments of the BFM apparatus can also be used to monitor bladder fullness during voiding and provide a signal which is used to determine when to cease self-voiding or stimulation (e.g., of the pudendal nerve) to cause such when the bladder is voided to an acceptable residual volume. In particular embodiments, the signal can be sent to a bladder control system such as that described in U.S. patent application Ser. No. 15/410,692 and used by the system to cease stimulation of pudendal nerve so as to cease voiding.

Referring now to the drawings, embodiments of an apparatus 110 and system 100 for measurement of bladder fullness will now be described. According to one embodiment depicted in FIGS. 1 and 2, a bladder fullness measurement (BFM) system 100 includes a BFM apparatus 110 and a controller 170 (described in more detail below). Apparatus 110 includes a base 120 comprising a flexible material, a rigid layer 130 attached to the base, a deformable membrane 140 positioned over and hermetically sealed to the rigid layer 130, and a pressure sensor 150. The base 120 is configured to be positioned in and attached (e.g., via suturing) to tissue T between the pubic bone PB and the bladder B. The base 120 may be configured to be positioned near the patient's pubic bone such that mechanical support provided by the pubic bone to the base prevents membrane 140 from being substantially deformed by force from tissue other than the bladder B. As used herein the term "substantially deform" means deformation in one or more dimensions of membrane 140 of more than about 10%, more preferentially, more than about 5%. In these and related embodiments, the base 120 may specifically be configured to conform to a contour C of the pubic bone so as to be mechanically supported by the public bone. According to one or more embodiments, the base may have a circular shape with a diameter 120D in a range from about 1.5 to 3.0 cm with larger and smaller diameters contemplated. The shape and diameter 120D of base 120 can be configured to place the base 120 at a desired location at or near the patient's pubic bone PB and bladder B including being positioned against a section of the public bone facing the patient's bladder.

In various embodiments, base 120 may be configured to be sutured or otherwise affixed to tissue T. According to one embodiment, this may be accomplished by the use of suture holes 121 placed at selected locations in the base 120. In additional or alternative embodiments, this may be accomplished by configuring base 120 to be sutured through by the passage of a surgical needle or other like device through the base. In these and related embodiments, the material properties of the base 120 are desirably configured to allow suturing through the base while minimizing tearing of the base from suturing (e.g., by passing the suture though the base) In particular embodiments, such tear resistance can be achieved by fabricating the base 120 from a fibrous mesh impregnated with an elastomer. In or more embodiments, the fibrous mesh may correspond to DACRON (woven or knitted) and the elastomer to silicone or polyurethane, with other fibrous materials (e.g., NYLON) and other elastomers known in the medical arts also considered. In specific embodiments for conferring tear resistance, the tear strength of the base material in a range of about 0.5 to 20 lbs/inch with specific embodiments of 0.75, 1, 2.5, 5, 7.5, 10, 12, 15 and 17.5 lbs/inch.

The rigid layer 130 may comprise various metals (e.g., stainless steel) or rigid polymers known in the art e.g. polycarbonate or PMMA (Poly(methyl methacrylate)). In many embodiments, rigid layer 130 has an approximate circular shape particularly those embodiments where the base has a circular shape. Other shapes are also considered and the shape may in some embodiments correspond to the shape of base 120. The rigid layer 130 may have a diameter 130D in a range from about 0.5 to 1 cm with larger and smaller diameter contemplated. Desirably, at least a portion of rigid layer 130 comprises a conductive material such as a metal or conductive polymer. That portion will now be referred to as a conductive portion herein conductive portion, 130c. Conductive portion 130c serves to make electrical contact between the pressure sensor 150 and a lead wire 160 or other electrical conduits so as to send signals from the sensor to an electrical device such as a controller 170 or transmitter. In particular embodiments, the lead 160 can be coupled to conductive portion 130c by means of a connector 165 in the form of a tab 166 having one or connector electrodes 167 which may contact with individual wires 168 of lead wire 160. Tab 166 or other connector 165 can be covered by an insulative cover 169 which may comprise an insulative polymer that is molded in place. The deformable membrane 140 is sealed to the rigid layer 130 so as to define a cavity 135 between the membrane and the rigid layer. The cavity 135 is filled with a fluid 137 such a mineral oil or silicone. The membrane 140 is positioned and configured to deform from force exerted by the bladder B against the membrane so as to exert a pressure on the fluid 137, with the pressure being correlated to a degree of fullness of the bladder. A desired level of deformability of the membrane 140 may be achieved by the selection of its dimensions (e.g., thickness) and the use of various deformable materials known in the material science arts such as metals and polymers including, various elastomers known in the art, e.g., silicone, polyurethanes and the like.

Figure 1A:
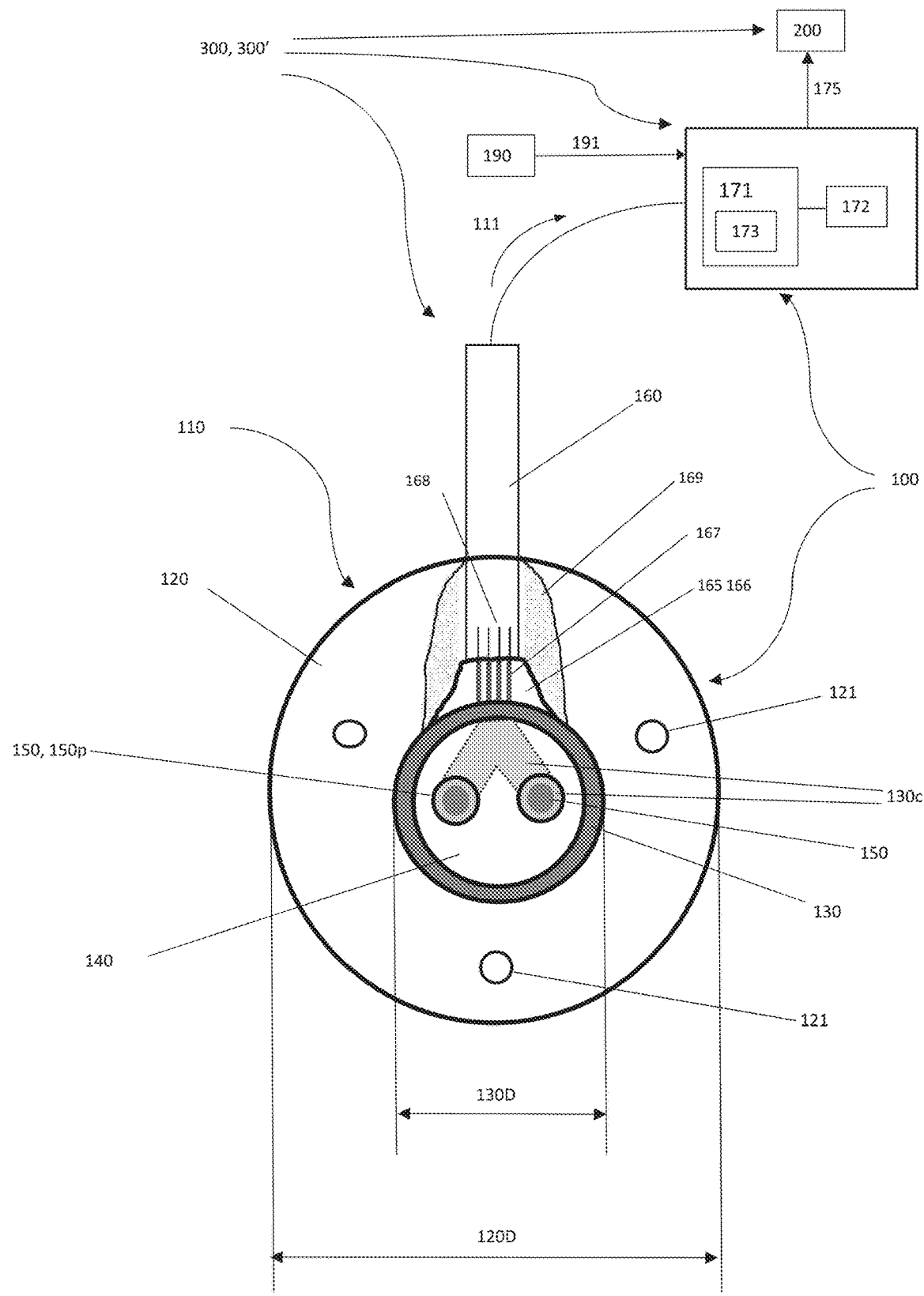
FIG. 1A illustrates an embodiment of a bladder fullness apparatus having multiple sensors.

According to one or more embodiments, pressure sensor 150 is positioned on a portion of the rigid layer 130 within the cavity such that it is able to measure the pressure of the fluid within the cavity 135. The sensor 150 is configured to generate a signal (electrical/analogue or digital) correlated to the pressure within the cavity which is in turn correlated to a degree of fullness of the bladder. Sensor 150 is electrically coupled to the conductive portion 130c of the rigid layer such that signals generated by the pressure sensor can be transmitted via conductive portion 130c to a controller or other electrical circuitry. The sensor 150 may be attached to the rigid layer 130 via various adhesives known in the art and may be electrically coupled to the conductive portion 130c by solder or other electrically conductive means. According to various embodiments, the pressure sensor 150 may correspond to one or more of a strain gauge, a solid state sensor or a MEMS-based sensor. In specific embodiments, the strain gauge may correspond to a Wheatstone bridge circuit known in the art. Also, according to some embodiments such as that shown in FIG. 1A, the sensor 150 may comprise a plurality of sensors 150p, positioned in one or more locations within the cavity. Use of a plurality of sensors 150p provides the benefit of a more uniform measurement of pressure within cavity 135 to account for any differences in pressure within the cavity 135 as well as providing redundancy should any individual sensor 150 fail after implantation.

Figure 3A:
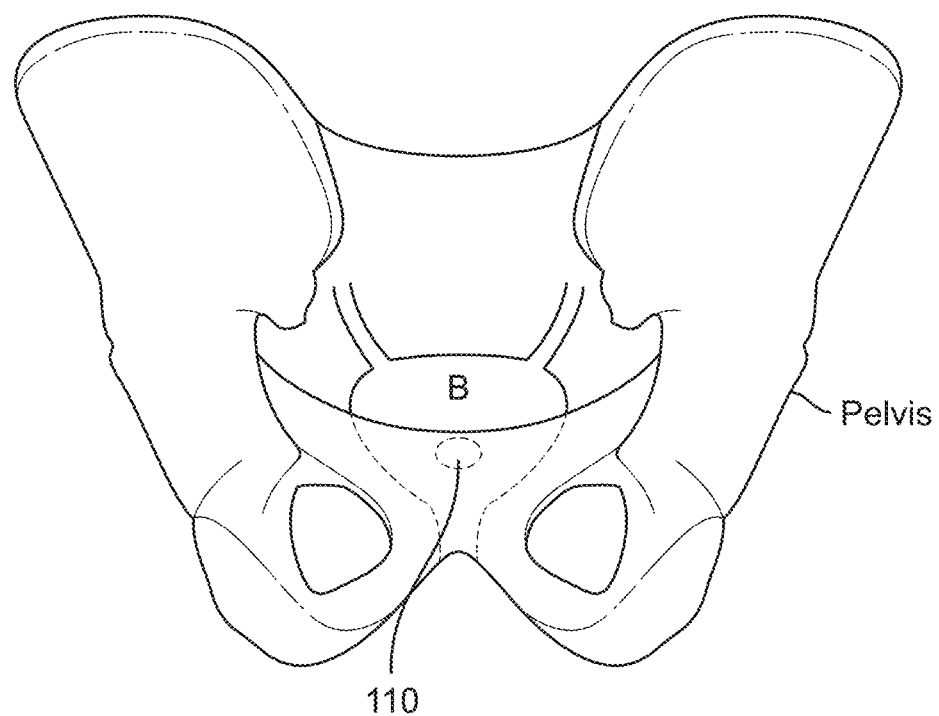
FIGS. 3A-3B illustrate placement of the bladder fullness measurement apparatus (BFMA) within the pelvic area of the patient.
Figure 3B:
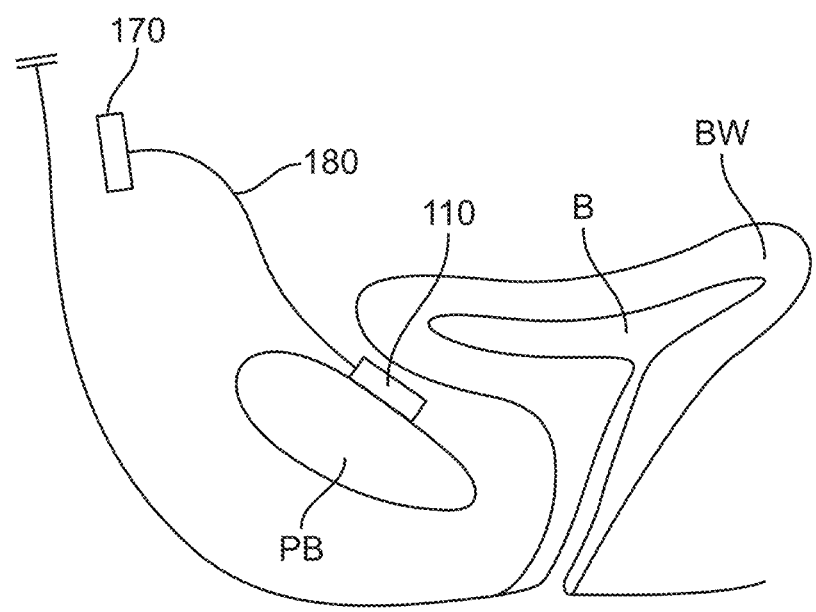
Figure 4A:
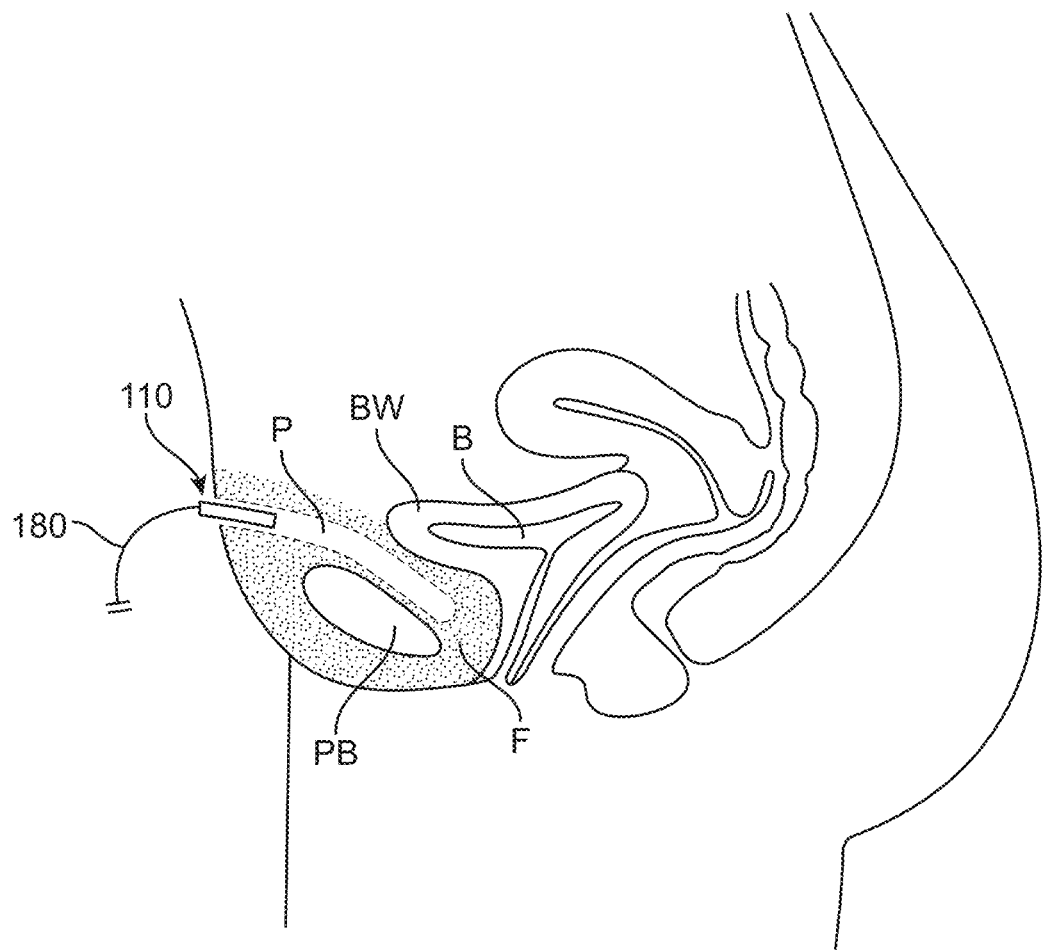
FIGS. 4A-4D illustrate placement of the BFMA in a surgical pocket between the pubic bone and the bladder wall.
Figure 4B:
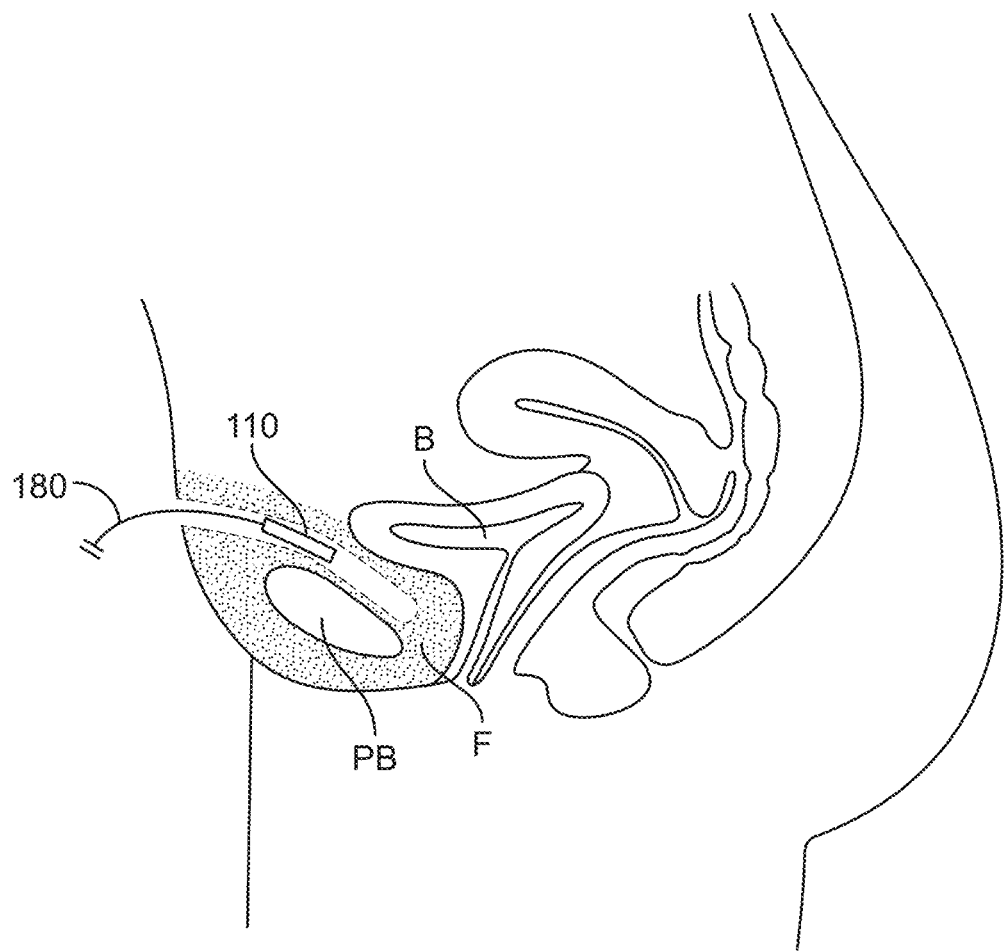
Figure 4C:
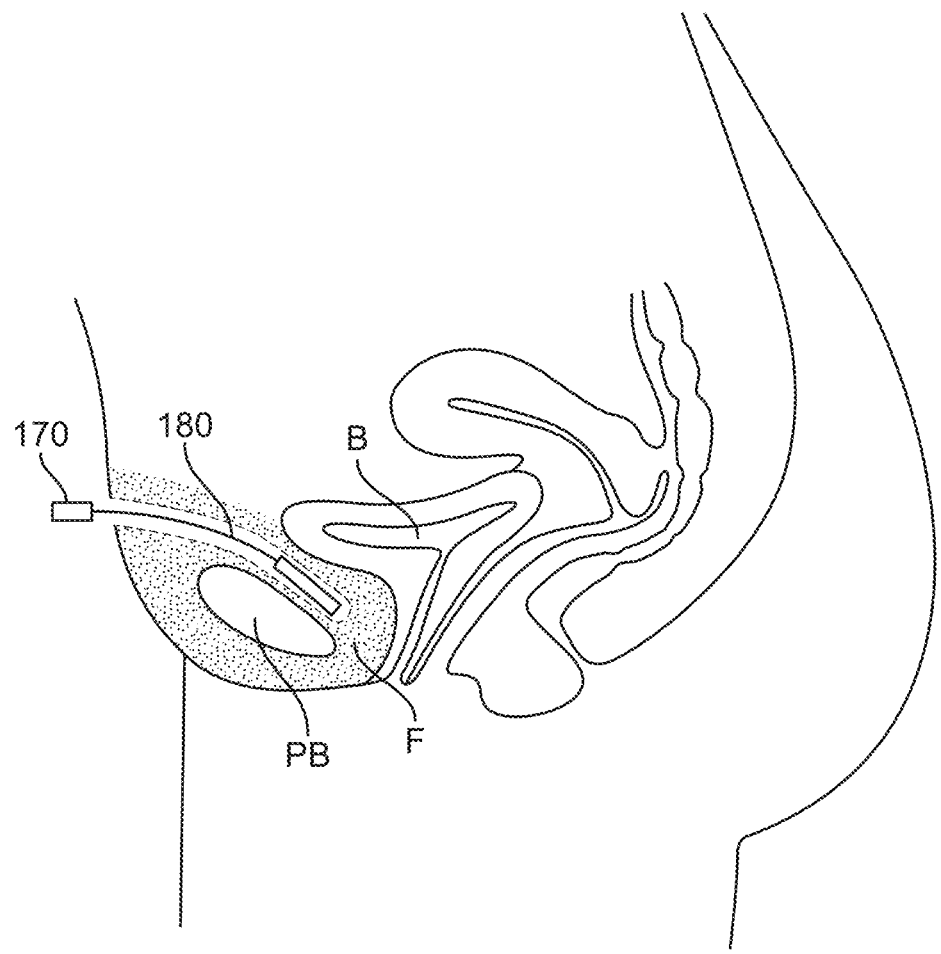
Figure 4D:
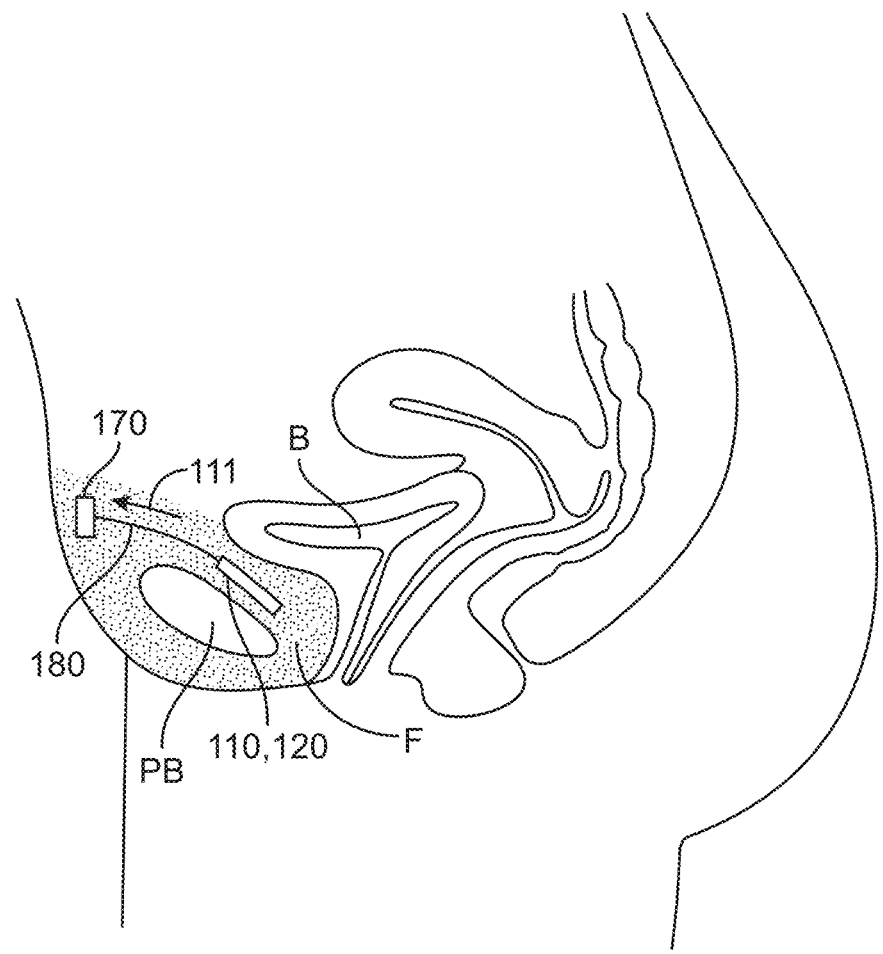

In many embodiments, system 100 includes a controller 170 for receiving signals 111 (also referred as output signals 11), which may be electrical or digital, from apparatus 110 and using information from the signals 111 to perform one or more functions related to the monitoring and control of a patient's urinary function. The controller 170 may be coupled (directly or operably) to the BFM apparatus via a lead wire or other electrical conduit 180 as is shown FIGS. 3b and 4a. According to one or more embodiments, controller 170 comprises logic resources 171 which may include or correspond to one or more of a microprocessor, application integrated circuit (ASIC) analogue device, state/machine device, or other logic resources known in the art. Controller 170 may also include or be operably coupled to memory resources 172 such as RAM, DRAM, SDRAM, SDR SDRAM, ROM, flash memory etc.; and a transmission means such as an RF transmission device. Typically, the controller 170 will contain logic in the form of electronic instruction sets which may be in the form of a software module 173 that is operable on microprocessor or other logic resources 171. Module 173 may include algorithms for controlling one or more aspects of urination. Further description of the use of controllers and algorithms for control of a patient's urinary function may be found in U.S. patent application Ser. No. 15/410,692, entitled "Systems And Methods For Patient-Enabled Bladder Control", which is incorporated herein by reference for all purposes. In alternative or additional embodiments, including those where controller 170 corresponds to an analogue device, the logic used by controller 170 (e.g., for utilizing signals from BFM apparatus 110 to perform one or more functions) may be programmed in hardware.

In particular embodiments, controller 170 is configured to receive an output signal(s) 111 from the BFM apparatus 110 and use the signal to determine whether a percentage change in the output signal 111 from the BFM apparatus 110 exceeds a predetermined threshold. The predetermined threshold is based on the percentage change between bladder volumes representing "empty" and a particular degree of fullness. Upon determining if the percentage change in an output signal received from the apparatus 110 exceeds the predetermined threshold, the controller 170 may perform one or more functions. Those functions may include the sending of a notification or alarm to the patient when the fullness of the bladder reaches a desired level (e.g., full, near full, etc.). The notification or alarm may be sent to a dedicated device worn by the patient that is in communication with the controller (wirelessly or otherwise) or to an external device such as a cell phone, tablet or like device. In addition, upon determining that the percentage change in the output received by the controller 170 exceeds the predetermined threshold, the controller may send a signal 175 cause an associated implant 200 to induce urination in the patient. Implant 200 may correspond to a pulse generator or other electrical neuro-stimulation device known in the art.

In some embodiments, the BFM apparatus 110 or system 100 may include an accelerometer 190 for sensing an orientation or position of the patient (e.g., standing, lying down, etc.) which may affect one or more of bladder pressure and/or a bladder fullness measurement. Typically, accelerometer 190 will be operatively coupled to controller 170 (or another controller not shown but contemplated by embodiment of invention) such that signals 191 generated by the accelerometer (encoding information on the patient orientation or movement) are received by the controller. In an embodiment of system 100 or apparatus 110 which includes an accelerometer, controller 170 can include logic (e.g., modules) for using signals from the accelerometer 190 to detect whether the patient is in a particular position for example, supine sitting, standing or a bent-over position. Controller 170 may then make adjustments for an amount of bladder fullness which result in a notice or alert being sent to the patient, e.g., regarding bladder fullness, need to urinate etc. (e.g., the level of bladder fullness which trigger such a notice or alert may be increased or decreased depending the patient's position, orientation, etc.). In particular embodiments, the controller 170 includes logic (e.g., in the form of modules 173) to account for sudden changes in the patient's orientation such that signals 111 from the BFM apparatus sensor 150 during that time are: i) gated out or otherwise not used by controller 170 in the determination of bladder fullness during the orientation change and a fixed period afterward; ii) are adjusted to reduce their impact on bladder fullness determination by the controller; and/or iii) are taken over a longer sampling period in making a bladder fullness determination by the controller whenever an orientation change is detected. In use, such embodiments provide for more accurate message being sent to the patient regarding the bladder and/or urination urgency status. In cases of the bent-over position, the controller may also send the patient an alert to sit up due to the increased pressure put on the bladder from being put in the bent-over position. The reasons being that such pressure may possibly result in urinary linkage (incontinence) or urine being forced back into the kidneys. In this way, embodiments of the invention including an accelerometer, provide for the reduced possibility of damage to the kidney as well as urinary leakage for patients who have lost the ability to urinate due to spinal injury or other cause such as multiple sclerosis.

According to various embodiments, accelerometer 190 may be directly affixed to the BFM apparatus 110 for example to base 120. Alternatively, it may be positioned external to the BFM apparatus and either coupled by wire or wirelessly. For external positioning embodiments, accelerometer 190 will typically be configured to wirelessly communicate with controller 170 (or other controller) and may either be implanted or worn externally by the patient. The wearable configurations for accelerometer 190 may correspond to a band worn around the patient's waist, arm or leg, or a skin adherent patch worn at one or more locations on the patient's body, e.g., arm, leg, torso, etc. In particular embodiments, multiple accelerometers 190 may positioned in multiple locations on the patient's body (e.g., lower leg, waist, neck, etc.) in order to make a more accurate determination of the patient's exact position/orientation (e.g., standing, sitting supine, and the like).

A description will now be provided of embodiments of methods for monitoring the fullness of a patient's bladder using one or more embodiments of the bladder fullness measurement (BFM) apparatus 10 described herein. One embodiment of such a method comprises positioning an embodiment of the BFM apparatus 110 between the patient's pubic bone PB and the bladder B such that the pressure sensor 150 is subjected to force from the patient's bladder (due to its degree of fullness) but not substantially effected by force from other tissue (e.g., other than the bladder). In many embodiments, this can be accomplished by positioning the back or base 120 of the BFM apparatus 110 so that it faces the pubic bone PB such that the base is mechanically supported by the pubic bone. Desirably, though not necessarily, the BFM apparatus 100 is fixedly attached to connective tissue adjacent or near the bladder wall such as fascia F. It may also be directly attached to the bladder. Such fixed attachment can be accomplished by suturing the base 120 to the fascia or bladder wall via one or more suture holes 121 in the base or other location on the apparatus. Also, according to some embodiments, the base 120 of apparatus 110 can be conformed (e.g., bent) or otherwise shaped by the surgeon to the curve C of the patient's pubic bone PB. These and related embodiments provide for the ability to use the patient's pubic bone as one approach for shielding the sensor apparatus from tissue forces other than that from the bladder. Base 120 may be pre-bent before implantation to a contour C matching or otherwise similar to that of the pubic bone or at the time of the implantation. Conformability of base 120 can be achieved by the use of conformable materials, such as various conformable polymers for all or a portion of base 120. In alternative or additional embodiments, all or a portion of apparatus 110 including base 120, can be configured to be foldable and unfoldable so that it can be inserted through tissue in a folded state so as to minimize the size of incision made to access the patient's bladder/pubic bone region and then unfolded into an expanded state once it is positioned at a desired implantation site in the bladder/pubic bone region.

In particular embodiments, base 120 may be configured to be folded, furled, or otherwise sufficiently flexible to be inserted through a standard size laparoscopic trocar so to allow for placement of base 120 at a desired implantation site using a laparoscopic surgical approach known in the minimally invasive surgical arts. Various approaches and embodiments for obtaining a foldable base 120 may include the use of shape memory super elastic alloys such as nickel titanium alloys an example including, NITINOL. Shaped memory alloys are deformable metal alloys which are capable of being heated treated so as to remember a shape they are held in during heat treatment. This shape is known as the memory or original shape. When cooled below a first transition temperature (e.g., a martensitic transition temperature for nickel-titanium alloys) they become super-elastic and can be readily deformed to assume a different shape (e.g., a deformed shape) from the memory shape. However when heated above the first transition temperature to a second transition temperature (e.g., austenitic transition temperature for nickel-titanium alloys) they reassume their original or memory shape. In this case, the memory shape for base 120 may correspond to the unfolded flat or slightly curved shape configured to be positioned near or adjacent the pubic bone, while the deformed shape corresponds to the folded or furled shape of the base for insertion and advancement through a trocar or other minimally invasive surgical introducer known in the art. Also, the second transition temperature may configured to be at or slightly below (e.g., within 5° C.) to that of the body temperature so that the once positioned within the body at a selected tissue site, the base will unfold to its memory shape from heating provided by contact with body tissue and/or body fluids. In some embodiments, the surgeon may irrigate base 120 with hot water at or above the transition temperature so as facilitate or accelerate the transition of the base to its unfolded state. In use, these and related embodiments, provide the benefit of reducing the incision size for implanting the apparatus 110 as well as allowing the surgeon to more easily manipulate and implant the apparatus in the body while the base is in its unfolded state.

In particular embodiments, the BFM apparatus 110 may be positioned in a pocket P created by the surgeon in the fascia F or other connective tissue between the pubic bone BP and the bladder wall BW. Referring now to FIGS. 4A-4D, in one approach for making such a tissue pocket, the surgeon creates the pocket P and then slides the apparatus into the pocket and then sutures the base 120 to the connective tissue. This thickness of the apparatus 110 and/or that of base 120 can be selected such that the surgeon need only create a pocket having a width of about 1 cm or less though, larger dimensions are also contemplated.

Once positioned at a selected location in tissue between the patient's pubic bone PB and bladder B, the BFM apparatus 110 may be coupled to a controller such as controller 170, which receives signals 111 from the apparatus corresponding to an amount of fullness of the bladder. Coupling may either be directly by a lead wire other electrical conduit or, wirelessly using an RF transmitter or other transmission means. In particular embodiments, the controller 170 may be part of or otherwise operably coupled to a urination control system 300 (aka urinary control system 300) which may include or be configured as a closed loop urination control system. In various embodiments, the BFM apparatus 110 may be implanted in an on or active state or switched to an active state from a sleep state (e.g., a low power state) or off state once implanted. Once implanted and activated, apparatus 110 sends signals 111 corresponding to the degree of fullness of the bladder to the controller 170. The controller may then use those signals 111 to perform one or more functions which may be associated with the patient's urinary function including, for example, those involved with monitoring and/or control of urinary function. In particular embodiments, signals 111 are used by the controller to initiate urination using a urinary control system such as a closed loop urinary control system 300' which may be associated with and/or operatively coupled to an implanted neuro-stimulation apparatus 200 which may be part of urinary control system 300. As such in these and related embodiments, urinary control system 300 can be configured to initiate and/or control urination in the patient based on signals 111 received from apparatus 110, which are used by controller 170 to cause neuro-stimulation device 200 to stimulate the patient's pudendal nerve (or other appropriate portion of their neuroanatomy) to initiate and/or control urination.

In various embodiments, the apparatus 110 may be implanted in a pre-calibrated state or may be calibrated after implantation as is discussed herein. It may also be implanted in an active state or switched to an active state once implanted as is discussed above. Once implanted and activated, the BFM apparatus 110 sends a signal to controller 170 corresponding to the degree of distention/fullness of the bladder to the controller (for embodiments that involve post implant calibration, logic. e.g., programming) used by the controller may be updated with the calibration value). The controller then uses that signal to perform one or more functions which typically will involve the patient's urinary function. According to one or more embodiments, the functions may include causing an associated implant 200 (e.g., an implanted pulse generator or other neuro-stimulation device) to perform a function (e.g. stimulation of the pudendal nerve) associated with initiating or performing a urinary function in the patient (e.g. contraction of the bladder) or sending a notification or alert to the patient. The notification or alert may be sent to the patient for example via a cell phone or PDA device operably coupled to or otherwise in communication with the controller (e.g., via RF communication). The notification or alert may related to one or more of the following: the degree of fullness of the bladder, an estimated time when the bladder will be full, and a need to urinate based on the degree of bladder fullness. The alert on the need to urinate may include a ranking of the need to urinate, such as immediately (e.g., next five minutes), moderate (e.g., next five to ten minutes), or low (e.g., next 15 to 30 minutes).

In one or more embodiments, the BFM apparatus 110 or system 100 may be calibrated after implantation so as to calibrate the signals 111 (which may be electrical or digital) generated by the BFM apparatus 110 to a specific amount of fullness of the bladder. In one implementation, calibration can be accomplished by filling the patient's bladder with a known volume(s) of fluid using a Foley or other urinary drainage catheter known in the art and then measuring the signal 111 produced by the BFM apparatus 110 in response. A calibration curve can be developed and data can be then downloaded to controller 170 or other logic resources coupled to the BFM apparatus 110 or system 100. Typically, several calibrations will be done over the first several months after implantation of the BFM apparatus 110 at a selected tissue site. The first calibration may be done soon after implantation and then subsequent calibrations may be done several months after implantation to account for a wound healing or related response in around the implanted apparatus 110. Such a wound healing response may alter the calibration of the apparatus by changing or otherwise affecting the deformability of the deformable membrane 140 and/or the amount of force exerted by the bladder against the apparatus 110, in particular to the membrane 140 and pressure sensor 150. In use, the performance of subsequent calibrations provide for the ability of accounting for changes in the output of the apparatus (e.g., in output signals 111) caused by the wound healing response or other physiologic adaption of the patient's body to apparatus 110, for example, protein, mineral, or cellular deposition, shifting position of apparatus within the patient's body or shifting positions of the patient's bladder and bone structure. This in turn provides the benefit of more consistent and thus improved measurements of bladder fullness by apparatus 110 over the implanted life of the apparatus. According to one or more embodiments, controller 170 may include logic (e.g., in the form of software or other electronic instruction set modules 173 herein modules 173) for determining: i) when the apparatus has come out of calibration; and then, ii) alert the patient or physician of the need to do to a subsequent calibration. The alert can be in the form of a message sent to an external communication device such as cell phone in the patient's possession or a message sent over the Internet or the cloud to the patient's doctor or other medical practitioner. In one or more embodiments, the logic used by the controller for determining when the apparatus is out of calibration may include an algorithm which analyzes changes in measured pressure over a selected length of time (e.g., days, weeks or months) and makes a determination based on those change. In particular embodiments, the change in measured pressure over time may correspond to a change in average measured pressure over time or a change in a moving average of measured pressure over time. Preferably, though not necessarily, the change in the average will be a statistically significant change (e.g., a p-value less than 0.05, more preferably than 0.01) using one or more statistical tests known in the art including, e.g., a T-test or an ANOVA test.

CONCLUSION

The foregoing description of various embodiments of the invention has been presented for purposes of illustration and description. It is not intended to limit the invention to the precise forms disclosed. Although embodiments are described in detail herein with reference to the accompanying drawings, it is to be understood that the concepts are not limited to those precise examples nor are the drawings necessarily drawn to scale. There may also be distinctions between the artistic renditions shown in the drawings and the actual apparatus due to drawing perspective, the drawings not necessarily being to scale, size constraints, manufacturing considerations and other factors. Also, there are multiple embodiments which are not necessarily shown in the drawings which are nonetheless contemplated by the present disclosure.

Further, many modifications, variations and refinements of the embodiments described herein will be apparent to practitioners skilled in the art including for example those skilled in the medical implant, sensor, biosensor, neuro-stimulation and urinary device arts. For example, embodiments of the BFM apparatus and system can be sized and otherwise adapted for various pediatric and neonatal applications as well as various veterinary applications. They may also be adapted for the urinary tracts of both male and females. Further, those skilled in the art will recognize, or be able to ascertain using no more than routine experimentation, numerous equivalents to the specific devices and methods described herein. Such equivalents are considered to be within the scope of the present invention and are covered by the appended claims below.

Also, elements, characteristics, or acts from one embodiment can be readily recombined or substituted with one or more characteristics or acts from other embodiments to form numerous additional embodiments within the scope of the invention. Moreover, elements that are shown or described as being combined with other elements, can, in various embodiments, exist as standalone elements. Further, for any positive recitation of an element, characteristic, constituent, feature, step etc., embodiments of the invention specifically contemplate the exclusion of that element, value, characteristic, constituent, feature or step. Hence, the scope of the present invention is not limited to the specifics of the described examples, but is instead limited solely by the appended claims.

What is claimed is:

1. An apparatus for monitoring the fullness of a bladder of a patient, the apparatus comprising:
   a base comprising a flexible polymer impregnated mesh material, the base configured to be positioned in and attached to tissue between the patient's pubic bone and the patient's bladder and to conform to a contour of the pubic bone so as to be mechanically supported by the pubic bone;
a rigid layer attached to the base, at least a portion of the rigid layer comprising a conductive material;
a deformable membrane positioned over and hermetically sealed to the rigid layer along a perimeter of the membrane, the membrane defining a cavity between the membrane and the rigid layer, the cavity filled with a fluid, the membrane positioned and configured to deform from force exerted by the bladder against the membrane so as to exert a pressure on the fluid, the pressure correlated to a degree of fullness of the bladder; and wherein the mechanical support provided by the pubic bone to the base prevents the membrane from being substantially deformed by force from tissue other than the bladder; and
a pressure sensor for measuring a pressure of the fluid within the cavity, the pressure sensor positioned on a portion of the rigid layer within the cavity, electrically coupled to the conductive portion of the rigid layer and configured to generate a signal correlated to a degree of distension of the bladder.

2. The apparatus of claim 1, wherein the pressure sensor comprises a strain gauge, a solid state sensor or a MEMS-based sensor.

3. The apparatus of claim 1, wherein the base includes attachment features for attaching the base to tissue.

4. The apparatus of claim 3, wherein the attachment features are suture holes.

5. The apparatus of claim 1, wherein the fluid is silicone oil or mineral oil.

6. The apparatus of claim 1, wherein the material properties of the base are configured to allow suturing through the base while minimizing tearing of the base from suturing.

7. The apparatus of claim 6, wherein the material property comprises a tear strength of the base.

8. The apparatus of claim 1, wherein the membrane comprises metal or a stainless steel.

9. The apparatus of claim 1, wherein the conductive portion of the rigid layer comprises conductive traces.

10. The apparatus of claim 1, further comprising an electrical connector coupled to the conductive portion of the rigid layer.

11. The apparatus of claim 10, further comprising an electrical lead coupled to the electrical connector for coupling the sensor to an electronic component or device.

12. The apparatus of claim 11, wherein the electronic component or device is a controller, a processor or microprocessor.

13. The apparatus of claim 1, wherein the membrane has a surface area in a range of about 10 to 50 times a surface area of the pressure sensor.

14. The apparatus of claim 1, further comprising an accelerometer for sensing an orientation of the patient.

15. The apparatus of claim 14, wherein the orientation includes at least one of a standing, supine, sitting or bent-over sitting position.

16. The apparatus of claim 14, wherein the accelerometer is coupled to the base.

17. The apparatus of claim 1, wherein the pressure sensor is operatively coupled to a controller and sends the signal correlated to the degree of bladder distention to the controller which utilizes the signal to perform a function or operation.

18. The apparatus of claim 17, wherein the controller causes an associated implant to perform a function when the signal exceeds a predetermined threshold.

19. The apparatus of claim 18, wherein the associated implant comprises a pulse generator.

20. An system for controlling or initiating urination in a patient, the system comprising:
a neuro-stimulation device for stimulating the patient's neuroanatomy to initiate or control urination in the patient;
the apparatus of claim 1; and
a controller operatively coupled to the neuro-stimulation device and the apparatus of claim 1, such that the controller receives the signal from pressure sensor and sends a signal to the neuro-stimulation device to perform a function to initiate or control urination when the signal from the pressure sensor exceeds a predetermined threshold.

21. The system of claim 20, wherein the neuro-stimulation device is implanted.

22. The system of claim 20, wherein the neuro-stimulation device includes a pulse generator.

23. The system of claim 20, wherein the function is stimulating a patient's pudendal nerve.

24. An apparatus for monitoring the fullness of a bladder of a patient, the apparatus comprising:
a base comprising a flexible material, the base configured to be positioned in and attached to tissue between the patient's pubic bone and the patient's bladder and to conform to a contour of the pubic bone so as to be mechanically supported by the public bone and to have a tear strength in a range of about 1 to 20 lbs/inch;
a rigid layer attached to the base, at least a portion of the rigid layer comprising a conductive material;
an insulative layer positioned over at least a portion of the conductive portion of the rigid layer;
a deformable membrane positioned over and hermetically sealed to the rigid layer along a perimeter of the membrane, the membrane defining a cavity between the membrane and the rigid layer, the cavity filled with a fluid, the membrane positioned and configured to deform from force exerted by the bladder against the membrane so as to exert a pressure on the fluid, the pressure correlated to a degree of fullness of the bladder; and wherein the mechanical support provided by the pubic bone to the base prevents the membrane from being substantially deformed by force from tissue other than the bladder; and
a pressure sensor for measuring a pressure of the fluid within the cavity, the pressure sensor positioned on a portion of the rigid layer within the cavity, electrically coupled to the conductive portion of the rigid layer and configured to generate a signal correlated to a degree of distension of the bladder.

25. An apparatus for monitoring the fullness of a bladder of a patient, the apparatus comprising:
a base comprising a flexible material, the base configured to be positioned in and attached to tissue between the patient's pubic bone and the patient's bladder and to conform to a contour of the pubic bone so as to be mechanically supported by the pubic bone:
a rigid layer attached to the base, at least a portion of the rigid layer comprising a conductive material;
a deformable membrane positioned over and hermetically sealed to the rigid layer along a perimeter of the membrane, the membrane defining a cavity between the membrane and the rigid layer, the cavity filled with a fluid, the membrane positioned and configured to deform from force exerted by the bladder against the membrane so as to exert a pressure on the fluid, the pressure correlated to a degree of fullness of the bladder; and wherein the mechanical support provided by the pubic bone to the base prevents the membrane from being substantially deformed by force from tissue other than the bladder; and a pressure sensor for measuring a pressure of the fluid within the cavity, the pressure sensor positioned on a portion of the rigid layer within the cavity, electrically coupled to the conductive portion of the rigid layer and configured to generate a signal correlated to a degree of distension of the bladder, wherein the material properties of the base are configured to allow suturing through the base while minimizing tearing of the base from suturing, the material properties comprise a tear strength of the base, and the tear strength of the base is in a range of about 1 lb/inch to about 10 lbs/inch.

26. An apparatus for monitoring the fullness of a bladder of a patient, the apparatus comprising:

a base comprising a flexible material, the base configured to be positioned in and attached to tissue between the patient's pubic bone and the patient's bladder and to conform to a contour of the pubic bone so as to be mechanically supported by the pubic bone;

a rigid layer attached to the base, at least a portion of the rigid layer comprising a conductive material, the conductive portion of the rigid layer including conductive traces;

an insulative layer positioned over at least a portion of the conductive traces or other conductive portion of the rigid layer;

a deformable membrane positioned over and hermetically sealed to the rigid layer along a perimeter of the membrane, the membrane defining a cavity between the membrane and the rigid layer, the cavity filled with a fluid, the membrane positioned and configured to deform from force exerted by the bladder against the membrane so as to exert a pressure on the fluid, the pressure correlated to a degree of fullness of the bladder; and wherein the mechanical support provided by the pubic bone to the base prevents the membrane from being substantially deformed by force from tissue other than the bladder; and a pressure sensor for measuring a pressure of the fluid within the cavity, the pressure sensor positioned on a portion of the rigid layer within the cavity, electrically coupled to the conductive portion of the rigid layer and configured to generate a signal correlated to a degree of distension of the bladder.

* * * * *